(12) United States Patent
Sheen et al.

(10) Patent No.: US 7,644,606 B2
(45) Date of Patent: Jan. 12, 2010

(54) PHOTOACOUSTIC SPECTROSCOPY SYSTEM AND TECHNIQUE FOR REMOTE SENSING OF EXPLOSIVES AND TOXIC CHEMICALS

(75) Inventors: Shuh-Haw Sheen, Naperville, IL (US); Apostolos C. Raptis, Downers Grove, IL (US); Hual-Te Chien, Naperville, IL (US)

(73) Assignee: UChicago Argonne, LLC, Argonne, IL (US)

( * ) Notice: Subject to any disclaimer, the term of this patent is extended or adjusted under 35 U.S.C. 154(b) by 276 days.

(21) Appl. No.: 11/699,146

(22) Filed: Jan. 29, 2007

(65) Prior Publication Data

US 2008/0180675 A1 Jul. 31, 2008

(51) Int. Cl.
*G01N 21/00* (2006.01)
*G01N 21/61* (2006.01)

(52) U.S. Cl. .................................... 73/24.02; 73/24.06
(58) Field of Classification Search ................ 73/24.02, 73/24.06
See application file for complete search history.

(56) References Cited

U.S. PATENT DOCUMENTS 5,161,408 A 11/1992 McRae et al.
5,834,632 A * 11/1998 Olender et al. ................ 73/40.7

OTHER PUBLICATIONS

M. Nägele and M.W. Sigrist. "Mobile laser spectrometer with novel resonant multipass photoacoustic cell for trace-gas sensing." Appl. Phys. B 70. 895-901 (2000).*

M. Webber, M. Pushkarsky, and C. K. Patel. "Optical detection of chemical warefare agents and toxic industrial chemicals: Simulation." Journal of Applied Physics 97, (2005).*

R. L. Prasad, R. Prasad, G. C. Bhar, S. N. Thakur. "Photoacoustic spectra and modes of vibration of TNT and RDX at CO2 laser wavelengths." Spectrochim Acta A Mol Biomol Spectrosc. 58(14):3093-102. Dec. 2002.*

"Detecting explosives with CO2 laser." The Hindu. Oct. 19, 2006.*

S. Bobrovnikov. "Development of methods and equipment for detection of explosives' vapors in the atmosphere with laser." Detection and Disposal of Improvised Explosives, 51-68. 2006.*

M. P. Pushkarsky, M. E. Webber, T. Macdonald, C. K. Patel. "High-sensitivity, high-selectivity detection of chemical warfare agents." Applied Physics Letters. 88. (2006).*

J. Gelbwachs. "Laser photoacoustic detection of explosive vapors." Optics in security and law enforcement; Proceedings of. SPIE Proceedings, vol. 108. p. 10-15. (1977).*

(Continued)

*Primary Examiner*—Lisa M Caputo
*Assistant Examiner*—Punam Patel
(74) *Attorney, Agent, or Firm*—Thomas W. Tolpin; Tolpin & Partners, PC

(57) ABSTRACT

A user-friendly photoacoustic spectroscopy (PAS) system and process (technique) provides an open-field PAS instrument, unit and device to remotely sense explosives, chemicals and biological agents. The PAS system and process can include: a pulsed tunable laser, such as a $CO_2$ laser, a reflector, such as a parabolic reflector, an acoustic reverberant resonator in which a microphone is installed, and a data acquisition and analysis system.

7 Claims, 9 Drawing Sheets

Remote PAS system

OTHER PUBLICATIONS

P. Hess. "Resonant Photoacoustic Spectroscopy." Topics in Current Chemistry. vol. 111. (1983).*

D. J. Brassington. "Photo-acoustic detection and ranging—a new technique for the remote detection of gases." J. Phys. D: Appl. Phys., 15. p. 219-228. (1982).*

Leite et al. "Photoacoustic Spectroscopy." Analytical Instrumentation Handbook. Ed. Galen Wood Ewing. 2nd ed. New York: Marcel Dekker, Inc. 1997. p. 596.*

"Liquid Explosives." GlobalSecurity.org. Nov. 8, 2006.*

Publication: S.H. Yonak and D.R. Dowling, "Gas-phase generation of photoacoustic sound in an open environment", J. Acoust. Soc. Am. 114(6) Pt. 1, pp. 3167-3178, Dec. 2003.

Publication: B. Perrett et al., "Remote photoacoustic detection of liquid contamination of a surface," Applied Optics, vol. 42, No. 24, pp. 4901-4908, Aug. 2003.

* cited by examiner

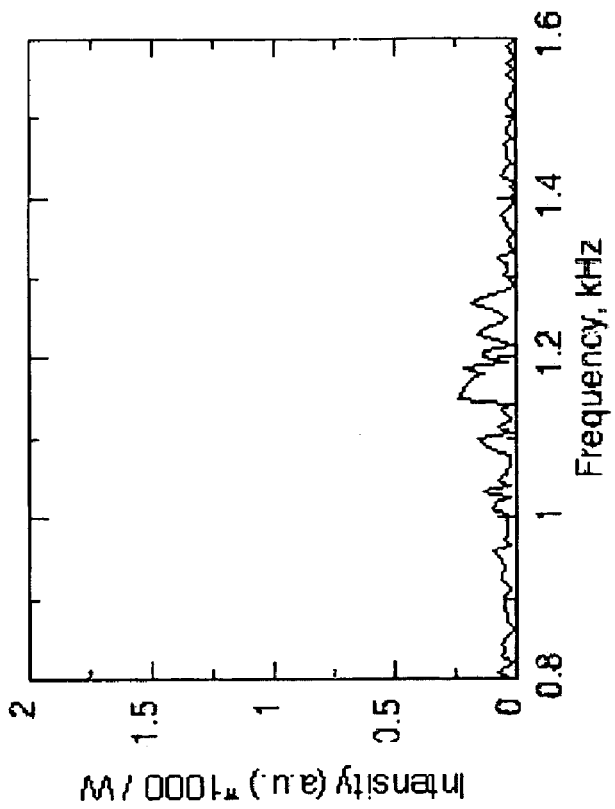
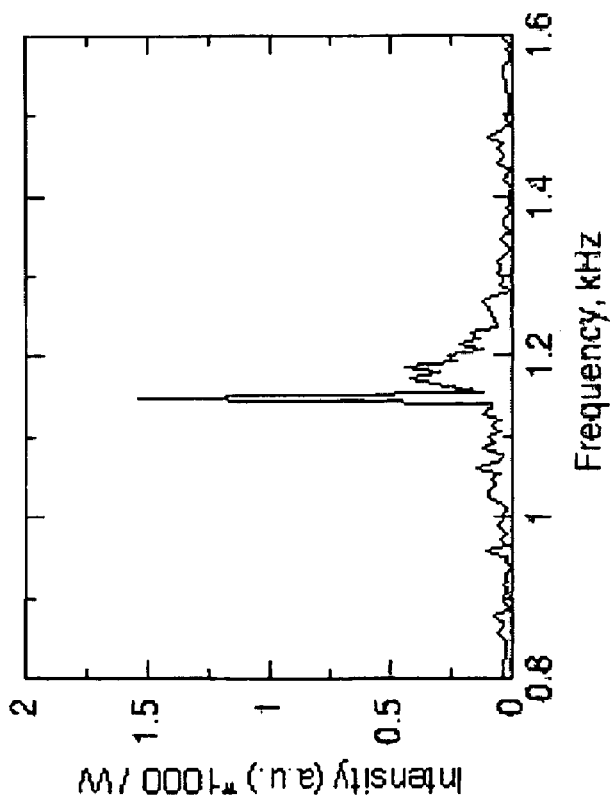
Fig. 6
Fig. 7

PHOTOACOUSTIC SPECTROSCOPY SYSTEM AND TECHNIQUE FOR REMOTE SENSING OF EXPLOSIVES AND TOXIC CHEMICALS

STATEMENT REGARDING FEDERALLY SPONSORED RESEARCH OR DEVELOPMENT

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

BACKGROUND OF THE INVENTION

This invention relates to photoacoustic spectroscopy, and more particularly, to photoacoustic spectroscopy (PAS) system for remote sensing of explosives and toxic chemicals.

In recent years, the dangers arising from possible terrorist attacks have become more imminent. New security systems have been installed at airports. Train stations and many bus depots have increased security. Government facilities and many commercial establishments have greatly increased security. Homeland Security and other government agencies and various companies have implanted new security measures and are looking for improved security systems and techniques.

It is desirable to remotely detect explosives, toxic chemicals, harmful biological agent, and other hazardous material so that the detected explosives, toxic chemicals, harmful biological agent, and other hazardous material can be safely removed and destroyed.

The technical difficulties of detecting explosives are: (1) most explosive have very low vapor pressure and, therefore, give poor signal-to-noise ratio, and (2) explosives typically are carried in concealed containers which further reduces their vapor concentration.

Over the years various systems and techniques (processes and methods) have been developed or suggested to detect explosives, toxic chemicals, harmful biological agent, and other hazardous material. Such prior systems and techniques to detect explosives, toxic chemicals, harmful biological agent, and other hazardous material, have met with varying degrees of success.

It is, therefore, desirable to provide an improved photoacoustic spectroscopy system and technique for remote sensing of explosives and toxic chemicals, which overcomes most, if not all of the preceding problems.

BRIEF SUMMARY OF THE INVENTION

An improved photoacoustic spectroscopy (PAS) system, technique, process and method are provided for remote sensing of explosives, toxic chemicals, biological agents, and other materials. Advantageously, the improved PAS system and technique (process or method) are easy to use, effective, efficient, and economical. The user friendly PAS system and technique can also be very sensitive and portable. Desirably, the improved PAS system and technique are particularly useful for homeland security and to help safeguard government buildings, airports, train stations, bus depots, industrial plants, power plants, petrochemical plants, refineries, factories, hotels, high rise buildings, schools, hospitals, homes, and other facilities. The improved PAS system and technique produced unexpected surprisingly good results.

The improved photoacoustic spectroscopy (PAS) system for remote sensing of explosives, toxic chemicals, and biological agents, or other material, can comprise various equipments as explained hereinafter which cooperate with each other to produce the desired analysis and results. In the PAS system, a tunable laser can be provided to transmit (deliver) optical energy comprising laser pulses at a selected frequency to a remote target comprising explosives, toxic chemicals, biological agents, or other hazardous material, causing acoustic signals to be emitted from the target. A pulse generator comprising a chopper operating at a frequency selected on the basis of background noise can be provided to generate pulses to the tunable laser. A sensor can be provided to detect (sense) acoustical signals from the target. A reflector can also be provided to receive and collect acoustic signals from the target and focus the acoustic signals to a focal area where the sensor is located. A resonator can be further provided to reduce (decrease) acoustic interference as well as to amplify the acoustic signals. The data acquisition and analysis equipment can be operatively connected (e.g. hard wired or by wireless) to the sensor, reflector, resonator, tunable laser, and pulse generator, and cooperates with the preceding to determine desired information about the target.

The tunable laser can be a pulsed laser, modulated laser, carbon dioxide ($CO_2$) laser, an ultraviolet (UV) laser, excimer laser, helium cadmium (HeCd) laser, solid state laser, diode laser, ion laser, or a fiber laser, and is preferably a carbon dioxide ($CO_2$) infrared (IR) laser.

The explosives, can be in solid, liquid, or gaseous form, and can be, but are not limited to: nitroglycerine (NG), ethylene glycol dinitrate (EGNG), dinitroltoluene (DNT), trinitrotoluene (TNT), or ammonium nitrate ($NH_4NO_3$).

A laser guiding and tracking system (equipment) can be operatively coupled (e.g. wireless connection or hardwired) to the tunable laser. The laser guiding and tracking system can comprise the sensor and a visible helium neon (He/Ne) laser.

The reflector can be a parabolic reflector with a diameter that is proportional to the distance to the target.

In one preferred system for detecting a biological agent, the laser comprises an ultraviolet (UV) laser, the reflector comprises a parabolic mirror and one or more optical sensors are positioned in the resonator.

The data acquisition and analysis equipment can comprise a central processing unit (CPU) and can have a screen to display real-time frequency-domain signals. The CPU can comprise a wireless microprocessor, hardwired microprocessor, laptop, portable computer, desktop computer, cell phone, iPod, Palm Pilot, Blackberry, mobile communications apparatus, or electronic handheld device.

In one preferred form, the resonator comprises a cylindrical tube resonator having a resonant frequency equaling (matching) the chopper frequency. In the illustrated embodiment, the resonator comprises an acoustic reverberant resonator. A microphone can be positioned in proximity, such as adjacent or inside, the resonator to receive the acoustic signals from the target. An optical fiber amplifier can be positioned downstream of the laser. A power meter can be operatively associated with the optical fiber amplifier or other equipment. The target can include surface contamination and can be gases, liquids, solids.

In one preferred form, the resonator comprises a tunable acoustic reverberant resonator and can be tuned to a specific resonant frequency and operates in an open field or area. The resonator can further comprise a negative expansion chamber having an area equaling the focal area of the reflector. The microphone can be mounted flush to an inside wall of the reflector at a position to optimize detection of the signal at the resonant frequency.

In the improved technique (method), a photoacoustic spectroscopy (PAS) process is provided for remote sensing of explosives, toxic chemicals, and biological agents, or other material. In the user friendly technique, optical energy comprising laser pulses can be transmitted (delivered) preferably at a selected frequency from a laser, most preferably a tunable laser, to a remote target comprising explosives, toxic chemicals, biological agents, or other material. Acoustic signals can be emitted from the target as a result of being the lased i.e. bombarded, struck or hit with the laser pulses. Background noise is scanned and a pulse generator comprising a chopper can be set and operated at a frequency in a region of least noise selected on the basis of the scanned background noise to generate pulses to the tunable laser. Acoustical signals can be detected (sensed) from the target with a sensor. The acoustic signals from the target can be received (collected) on a reflector and focused to a focal area in which the sensor located. Desirably, acoustic interference can be reduced (decreased), such as with a resonator, and the acoustic signals can be amplified. The resonator can be adjusted to resonate at the frequency of the chopper. Information about the target can be determined, such as with data acquisition and analysis equipment.

The PAS process (technique) can be used to detect explosives, chemicals, such as toxic chemicals, gases, such as trace gases, liquids, solids, biological agents, e.g. diseases, poisons, surface contamination, and other hazardous material.

A more detailed explanation of the invention is provided in the following detailed descriptions and appended claims taken in conjunction with the accompanying drawings.

BRIEF DESCRIPTION OF THE DRAWINGS

FIG. 6 is a chart of TNT detected with the laser on.

FIG. 7 is a chart of TNT detected with the laser off.

DETAILED DESCRIPTION OF THE INVENTION

The following is a detailed description and explanation of the preferred embodiments of the invention and best modes for practicing the invention.

Figure 1:
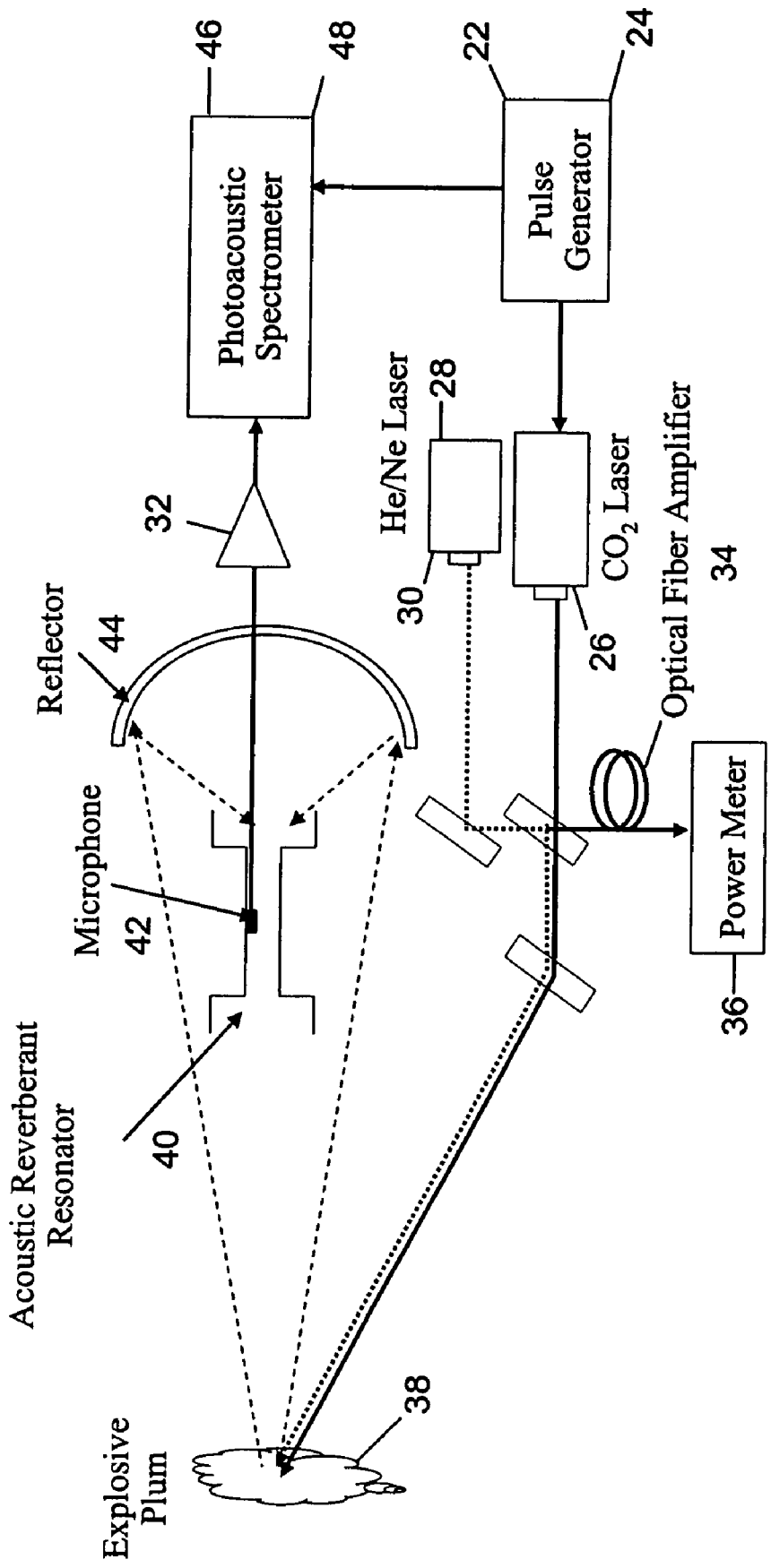
FIG. 1 is a schematic diagram of a photoacoustic spectroscopy (PAS) system and technique providing a remote sensing instrument, equipment, process and method in accordance with principles of the present invention.

FIG. 1 illustrates a photoacoustic spectroscopy (PAS) system 20 and technique, which provides an instrument, equipment, device, process and method for remote sensing of explosives, toxic chemicals, biological agents, and other materials. The PAS system and technique can have a pulse generator 22 with a chopper 24, a laser 26, a laser guiding and tracking system (equipment) 28 which can comprise a visible helium neon (He/Ne) laser 30 and a sensor 32, an optical fiber amplifier 34, a power meter 36, a target 38 which can comprise an explosive plum, an acoustic reverberant resonator 40 with a cylindrical tube, an acoustic transducer comprising a microphone 42, a reflector 44, and data acquisition and analysis equipment 46 which can comprise a photoacoustic spectrometer 48 and a central processing unit (CPU) with a monitor or screen and keys and a printer.

In the PAS system, the laser, which can be a tunable laser, can be provided to transmit (deliver) optical energy comprising laser pulses at a selected frequency to a remote target comprising explosives, toxic chemicals, biological agents, or other hazardous material, which can cause acoustic signals to be emitted from the target. Various types of laser can be used, such as a tunable laser, pulsed laser, modulated laser, carbon dioxide ($CO_2$) laser, an ultraviolet (UV) laser, excimer laser, helium cadmium (HeCd) laser, solid state laser, diode laser, ion laser, or a fiber laser, and preferably a carbon dioxide ($CO_2$) infrared (IR) laser. Carbon dioxide ($CO_2$) lasers use the energy-state transitions between vibrational and rotational states of $CO_2$ molecules to emit at long infrared (IR), about 10 μm, wavelengths and can maintain continuous and very high levels of power. Helium neon (HeNe) lasers have an emission that is determined by neon atoms by virtue of a resonant transfer of excitation of helium and can operate continuously in the red, infrared and far-infrared regions and emit highly monochromatic radiation. Excimer lasers are rare-gas halide or rare-gas metal vapor lasers emitting in the ultraviolet, that operate via the electronic transitions of molecules. Nitrogen lasers are an excellent source of high intensity, short pulse, ultraviolet radiation. Helium cadmium (HeCd) lasers are relatively economical, continuous-wave sources for violet (442 nm) and ultraviolet (325 nm) output. Solid state lasers use a transparent substance (crystalline or glass) as the active medium, doped to provide the energy states necessary for lasing and are used in both low and high power applications. Diode lasers use light-emitting diodes to produce stimulated emissions in the form of coherent light output. Ion lasers function by stimulating the emission of radiation between two levels of an ionized gas and can provide moderate to high continuous-wave output of typically 1 mW to 10 W. Tunable diode lasers can be adjusted to emit one of several different wavelengths. Fiber lasers use optical fibers doped with low levels of rare-earth halides as the lasing medium to amplify light.

The pulse generator and chopper preferably operates at a frequency selected on the basis of background noise to generate pulses to a tunable laser. Optical choppers are mechanical or electronic devices which intercept a light beam on a periodic basis, such a like a strobe, i.e. optical choppers are mechanical or electronic devices that pass and then interrupt a beam of light for a known brief interval. Optical modulators vary the amplitude and phase of a light beam, e.g., from a laser.

The sensor can detect (sense) acoustical signals from the target. The reflector can receive and collect acoustic signals from the target and focus the acoustic signals to a focal area where the sensor is located. The resonator can reduce (decrease) acoustic interference as well as to amplify the acoustic signals.

The data acquisition and analysis equipment can be operatively coupled and connected (e.g. hard wired or by wireless) to the sensor, reflector, resonator, tunable laser, and pulse generator. The data acquisition and analysis equipment can determine desired information about the target. The data acquisition and analysis equipment can comprise a photoacoustic spectrometer and/or a central processing unit (CPU) and can have a screen to display real-time frequency-domain signals. The CPU can comprise a wireless microprocessor, hardwired microprocessor, laptop, portable computer, desktop computer, cell phone, iPod, Palm Pilot, Blackberry, mobile communications apparatus, or electronic handheld device.

Figure 2:
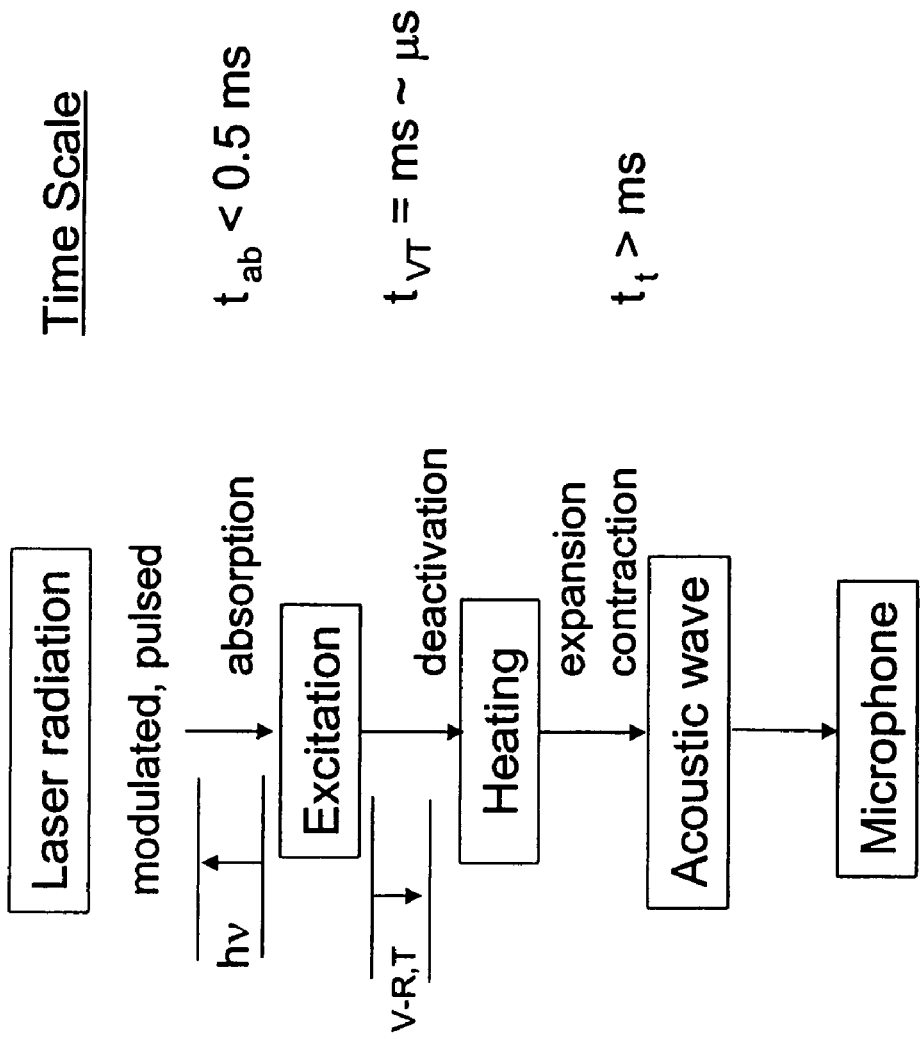
FIG. 2 is a schematic diagram of the PAS principle.

As shown in FIG. 2, the PAS principle can comprise laser radiation, which an be modulated or pulsed, absorption of the laser radiation on the target, excitation of the target material, deactivation, heating, expansion, contraction, transmitting and or emitting an acoustic wave from the target, and detecting the acoustic wave with a microphone.

Figure 3:
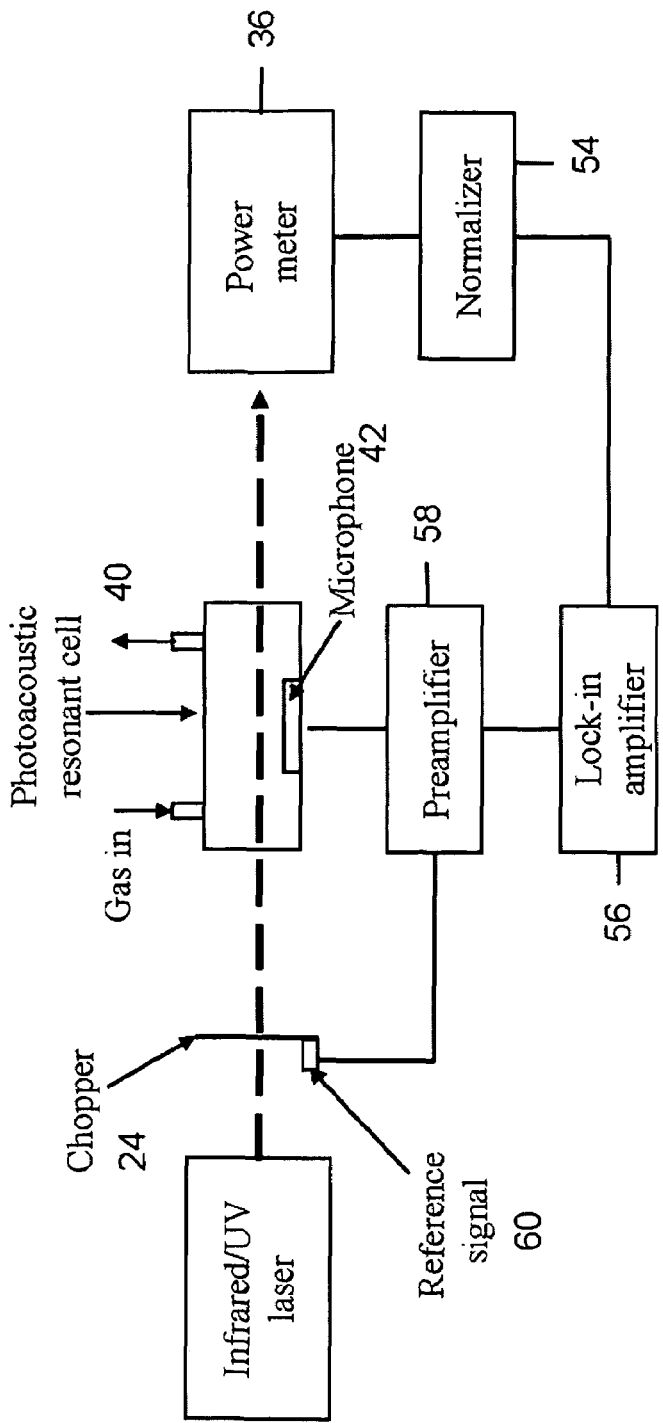
FIG. 3 is a schematic diagram of a Prior Art typical laboratory PAS setup.
Figure 4:
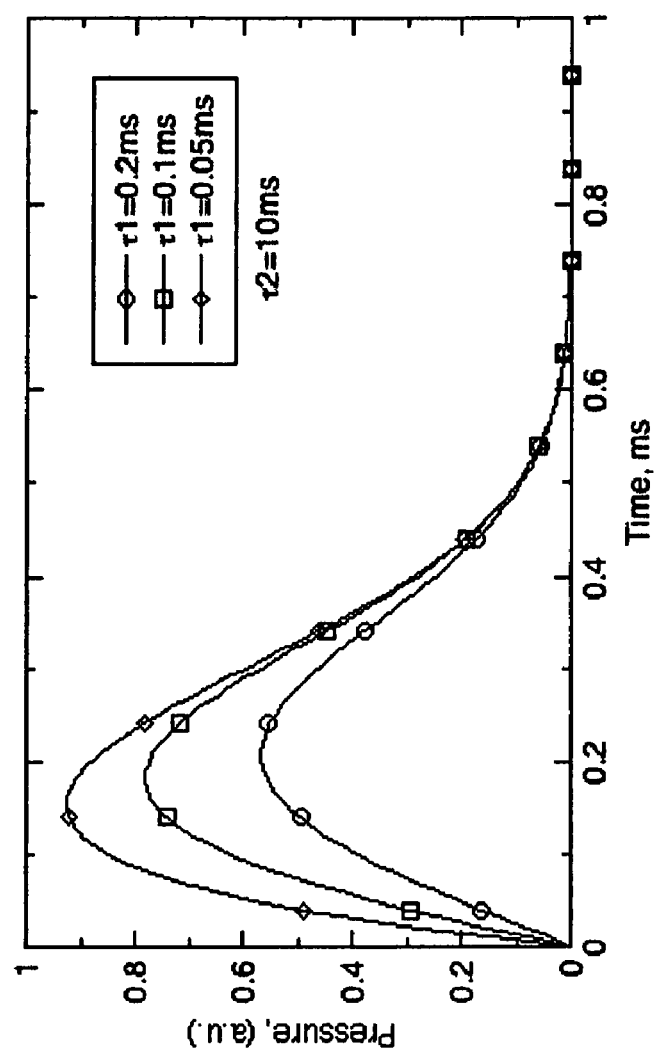
FIG. 4 is a chart of characteristic of a PAS signal.

A typical laboratory PAS setup as shown in FIG. 3 can include a chopper 24, a laser 26, such as an infrared (IR) or ultraviolet (UV) laser, a photoacoustic resonant cell (resonator) 40, a microphone 42, a power meter 36, a normalizer 54, a lock-in amplifier 56, a preamplifier 58, and a reference signal 60.

The PAS capabilities can include: remote sensing capability (laser based) with spectroscopic selectivity and sensitivity, real time analysis (no sampling involved), ranging capability, applicable to all phases of material, suitable for opaque materials, nondestructive, portable and relatively inexpensive.

The PAS technique for remote detection of explosive can overcome various challenges: poor signal-to-noise ratio and interference from environmental noise. Poor signal-to-noise ratio can result from extremely low vapor pressures for most explosives. In air under ambient conditions: ethylene glycol dinitrate (EGDN) is 50 ppm, nitroglycerine (NG) is 1 ppm, ammonium nitrate ($NH_4NO_3$) is 10 ppb, and trinitrotoluene (TNT) is 2 ppb. Poor signal-to-noise ratio can also result from open field sound propagation (e.g. an absorption loss of approximately 1 dB/1 m for 100 kHz signals in ambient air with 70% relative humidity). Interference from environmental noise can include background ambient noise and echoes from nearby objects.

A carbon dioxide ($CO_2$) laser can be used for detecting explosives. At an infrared (IR) wavelength in micrometers of 9.4 μm, nitroglycerine (NG) has a minimum detectable concentration of $0.055 \times 10^{-2}$ ppm/mW. At an infrared (IR) wavelength in micrometers of 11 μm, nitroglycerine (NG) has a minimum detectable concentration of $0.028 \times 10^{-2}$ ppm/mW. At an infrared (IR) wavelength in micrometers of 9.4 μm, ethylene glycol dinitrate (EGDN) has a minimum detectable concentration of 2.5 ppm/mW. At an infrared (IR) wavelength in micrometers of 11 μm, ethylene glycol dinitrate (EGDN) has a minimum detectable concentration of 1.5 ppm/mW. The —$NO_2$ has an absorption bands near 6 μm, 9-11 μm, and 11-12 μm, while water has absorption bands in 5-8 μm.

The reflector can be a parabolic reflector. The illustrated parabolic reflector can provide detection in the forward direction, focus signals to a focal region of about one wavelength in diameter, and provide a signal gain proportional to the reflector diameter.

The preferred acoustic resonator can isolate the microphone from the ambient environment. The preferred acoustic resonator can also provides amplification to resonant signals and provide for frequency analysis.

FIGS. 6 and 7 illustrates the PAS of $SF_6$ detected from 1.8 m away with a $CO_2$ laser line of 10.6 P (20), a laser power of 1.5 W, a chopper frequency of 1.2 kHz, and a $SF_6$ gas leak rate of 20 sccm.

Figure 8:
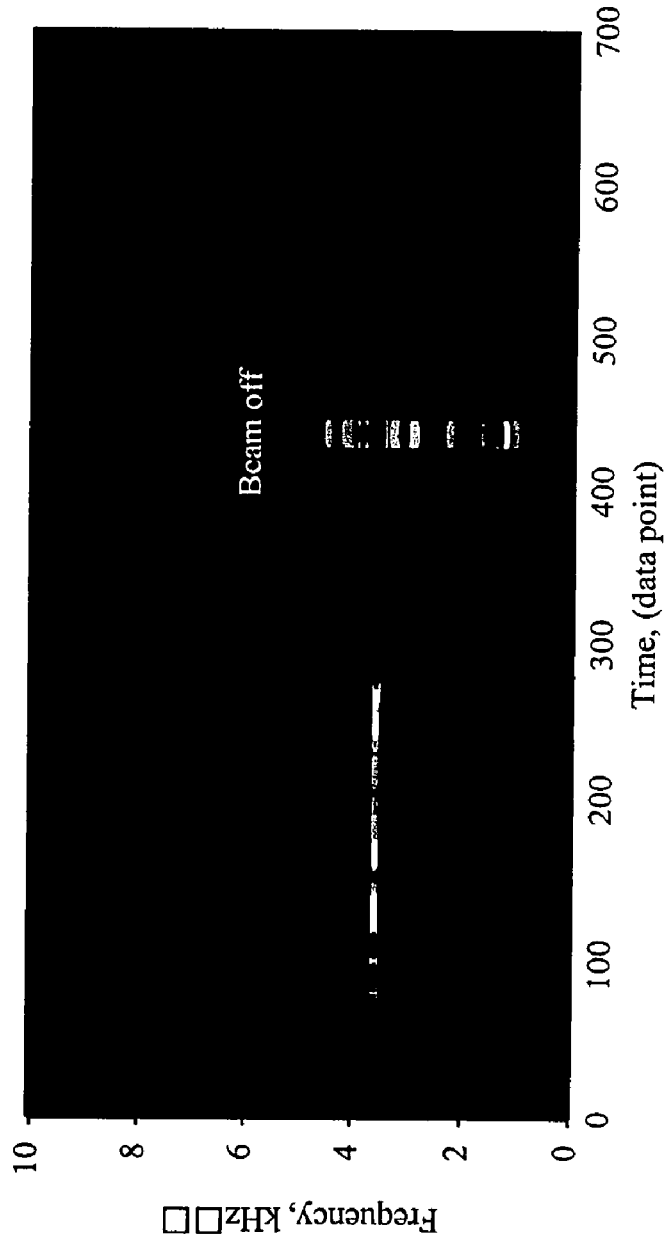
FIG. 8 is a chart of continuous real-time acoustic spectra.

FIG. 8 is a continuous real-time acoustic spectra for a remote sensing distance of 1.8 m, a laser line of 10.6 P (20), a laser power of 1.5 W, a $SF_6$ gas leak rate of 20 sccm, and acoustic frequencies of 1.2 kHz, 3.8 kHz, 4.9 kHz, and 6 kHz.

Figure 9:
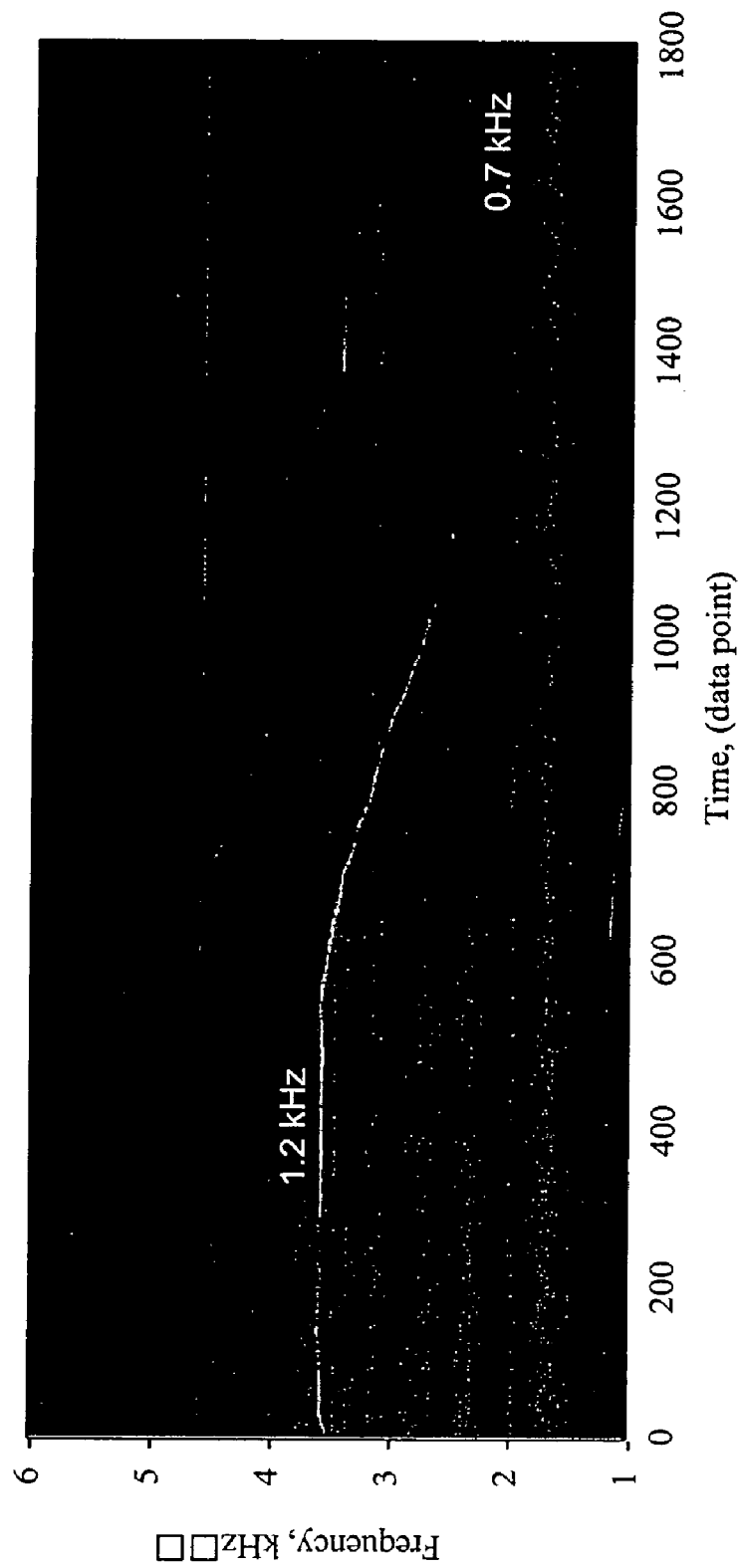
FIG. 9 is a chart showing the effect of chopper frequency on PAS.

FIG. 9 illustrates the effect of chopper frequency on PAS when the chopper frequency varies from 1.2 kHz to 0.7 kHz.

Figure 10:
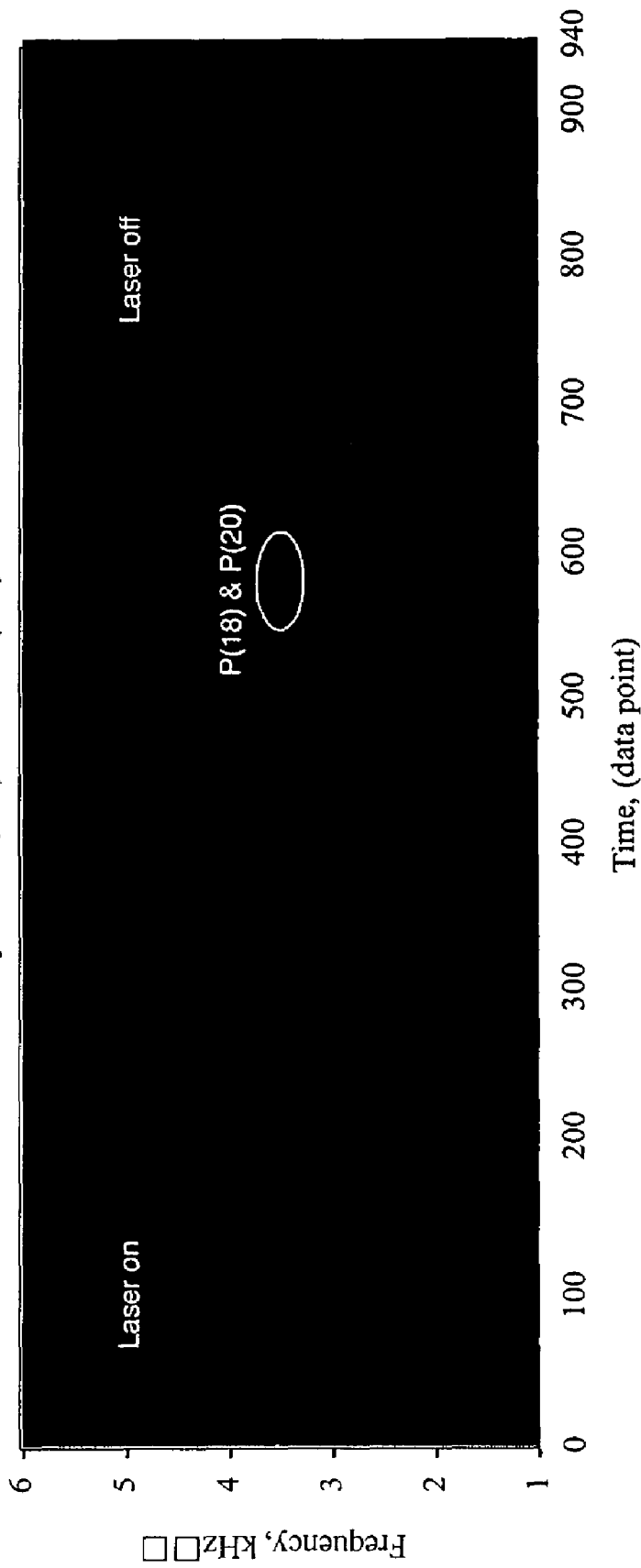
FIG. 10 is a chart of PAS selectivity.

FIG. 10 illustrates PAS selectivity when with the scan of the laser across 10.6 lines [P(8) to P(28)] and the PAS detected at P(18) and P(20)].

The photoacoustic spectroscopy (PAS) system and process provides a remote sensing instrument, apparatus and method (process) based on a PAS technique. The PAS system and process (technique) provides user friendly equipment and an easy method to detect explosives, toxic chemicals, and biological agents. The underlying principle of the PAS technique is to excite sample molecules with a pulsed laser tuned to a specific absorption line of the molecules and then to detect the induced acoustic signals produced during a molecular relaxation process. This PAS technique can be referred to as the thermal-piston effect. Its spectrum, acoustic peak pressure versus the laser frequency, is closely related to optical absorption spectrum and has a similar spectroscopic selectivity.

The PAS system and process also provides an open-field PAS instrument, unit and device that enables one to perform remote sensing of explosives, chemicals and biological agents. Major components of the PAS system and process can include (1) a pulsed tunable laser (e.g. a $CO_2$ laser for explosives and toxic chemicals), (2) a parabolic reflector, (3) an acoustic reverberant resonator in which a microphone is installed, and (4) a data acquisition and analysis system. Each component can perform the functions as described hereinafter.

A pulsed tunable laser can deliver (transmit) optical energy of selected frequency to a remote target area. Because the laser can be used is in the infrared region, a laser guiding and tracking system can be integrated into the laser system. The laser guiding and tracking system can comprise a visible He/Ne laser and an optical sensor to detect the reflection from the target object.

The parabolic reflector can receive and collect acoustic signals in the forward direction and focus the signals to the focal area where the acoustic sensor is positioned. The diameter of the reflector can determine the detection range.

The acoustic reverberant resonator can reduce (decrease) acoustic interference caused by the environmental noise and can also amplify the photoacoustic signals. The preferred design of the resonator is a cylindrical tube with adjustable length.

The data acquisition and analysis system can be a PC-based system. The acoustic signals that are synchronized with laser pulses can be analyzed for both time- and frequency-domain information, from which the location, identification, composition, and concentration of the target chemical are determined.

Major applications and uses of this PAS system and process (technique) can include: remote detection of (1) explosives, (2) toxic chemicals, and (3) biological agents, which can be present in the form of vapor, aerosol, or surface contamination in either liquid or solid phase. For the case of detecting surface contamination, the probing laser can also act, serve and provide a heat source to evaporate contamination from surface. Specific arrangements for different applications of the PAS system and process can be used.

In one preferred system and process (technique) to detect explosives, a $CO_2$ infrared (IR) laser is used to help identify, detect, and characterize the explosives because most explosives are mainly nitroaromatic compounds that have distinct IR absorption lines around 10 μm. For example, absorption lines for nitroglycerine (NG), ethylene glycol dinitrate (EGDN), and dinitrotoluene (DND) are between 9.4 μm and 11 μm. The PAS system and process can be used to detect explosives that are present in the ambient air or on the surface of a concealed container or vehicle.

In the PAS system and process to detect toxic chemicals, the selection of the laser depends on specific target chemicals of interest. Further use of the PAS system and process include pollution monitoring such as detection of NOx as well as leak detection for industrial processes such as pipeline leaks.

The PAS system and process (technique) can also be used to detect biological agents, most preferably with a UV laser. Preferably, such a PAS system and process can also detect (sense) acoustics and fluorescence light from the bioaerosol. Desirably, for such use, the parabolic reflector can be replaced by a parabolic mirror and additional optical sensors can be installed inside the resonator.

Figure 5:
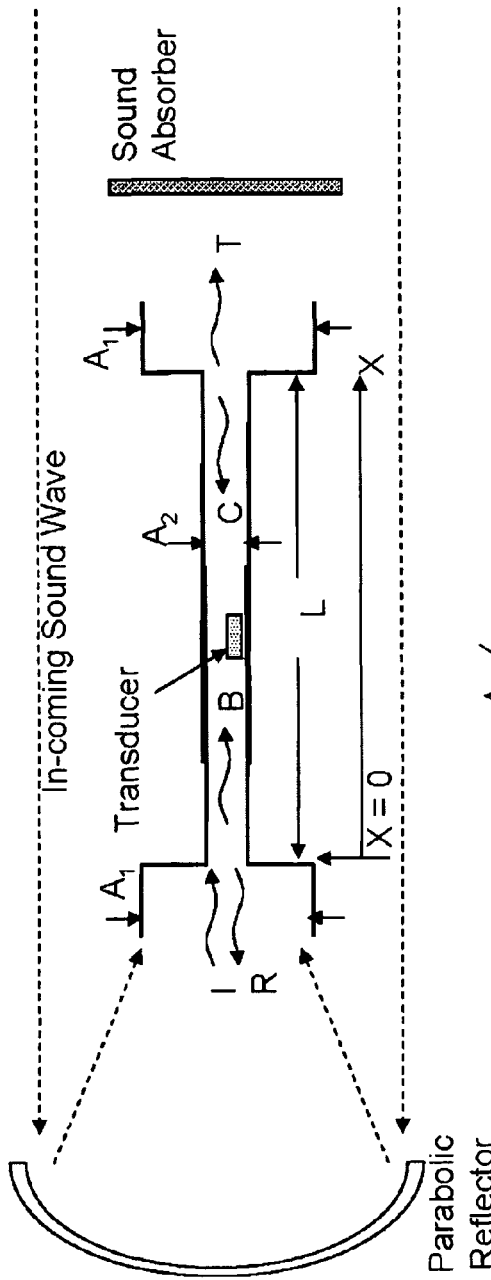
FIG. 5 is a schematic diagram an acoustic reverberant resonator and mathematical formulas related thereto.

As shown in FIG. 5, one of the components of the remote photoacoustic system can be an open-field acoustic resonator that comprises a parabolic reflector and a reverberant resonator. One of the benefits of using such a reflector is to focus acoustic signals. If one positions a microphone at the focal point, one would expect to receive the acoustic signals with a gain of $A_R/A_M$ where $A_R$ and $A_M$ are areas of reflector and microphone, respectively. Of course, this simple gain is valid only if the incoming acoustic waves spread over the entire reflector and the focal area has a similar dimension as the microphone. In case of remote sensing, we can assume that the incoming waves cover the entire reflector, but the area of the focal point needs to be determined by measurement.

To enhance detection sensitivity, a reverberant resonator can used and tuned to a specific resonant frequency and operate in open field. The resonator adopts the design of a negative expansion chamber illustrated in FIG. 5, in which the area $A_1$ will match the focal area of the reflector and $A_2$ will be the minimal size that a microphone can be flush mounted to the inside wall. Considering plane acoustic waves propagating from left to right, the pressure wave intensities in three regions can be expressed as follows:

$$P_1 = Ie^{i\omega(t-x/C)} + Re^{i\omega(t+x/C)} \quad x<0$$

$$P_2 = Be^{i\omega(t-x/C)} + Ce^{i\omega(t+x/C)} \quad 0<x<l$$

$$P_3 = Te^{i\omega(t-x/C)} \quad l<x \quad (1)$$

where I, R, and T are intensities of incident, reflected, and transmitted pressure waves, respectively; B and C are intensities of forward and backward propagating waves; and C is the sound velocity and $\omega$ the radial wave frequency. Applying boundary conditions, continuity of mass flux and energy flux, at X=0 and l and solving P in terms of I, one obtains an expression, Eq. 2, under the assumption that $A_1 \gg A_2$ $$|P|^2 = I^2 \frac{\left(\frac{A_1}{A_2}\right)^2 \sin^2\omega(l-x)/C}{\cos^2\omega l/C + \frac{1}{4}\left(\frac{A_1}{A_2}\right)^2 \sin^2\omega l/C} \quad (2)$$

Now, if one picks a length $l=n\lambda/2$, where n is an integer and $\lambda$ is the wavelength, Eq. 2 can be reduced to $$P = I\left(\frac{A_1}{A_2}\right)\sin\omega x/C \quad (3)$$

Based on Eq. (3), when $x=1-1/2n)l$, P becomes maximum and equals to I $(A_1/A_2)$. Based on the model, if we select a cylinder of l=8.6 cm and install the microphone at x=4.3 cm, we will be able to optimize the detection of a signal at 40 kHz.

As indicated above, the invention pertains to a remote sensing system, instrument, and process (method) based on photoacoustic spectroscopy (PAS) technique. It also relates to application of the instrument to detection of explosives, toxic chemicals, and biological agents.

Advantageously, the PAS system and process leads to a remote sensing field instrument for detecting trace gases, liquids and solids. The instrument may be used for environmental monitoring, leak detection of industrial processes, and explosives detection. The PAS system and process seeks to solve the problem of detecting explosives from a remote distance. The technical difficulties of detecting explosives are (1) most explosives having very low vapor pressure and thus giving very poor signal-to-noise ratio and (2) explosives typically being carried in concealed containers, further reducing their vapor concentration.

In the government sector, the PAS system and process can satisfy the immediate needs of protecting homeland security from terrorist attacks. The PAS system and process instrument provides the capability of non-destructively interrogating suspected explosive containers and devices from a safe distance.

For industrial processes, the PAS system and process can be used as a continuous detection and monitoring instrument for process integrity and emissions. For example, the PAS system and process can be used for remote detection of natural-gas pipeline leaks. Some of the many advantages of this PAS system and process over existing techniques, such as X-ray and mass-spectrometry, are its portability, simplicity and sensitivity.

There are many significant aspects of the PAS system and process including: (1) the total system, (2) the operation of the system (wavelengths and pulse frequencies used), and (3) application fields of the system and process.

Some of the key advantages of this PAS system and process are: (1) the ability to detect molecules associated with many typical explosives remotely, and (2) the ability to detect such molecules that are not in the gaseous state (e.g. residues on explosive packaging or silo structures are detectable by this technique).

Among the many other advantages of the PAS system and technique (process and method) are:
1. Outstanding performance.
2. Superior instrument.
3. Superb system.
4. Excellent technique.
5. Better results.
6. User friendly.
7. Reliable.
8. Readily transportable.
9. Light weight.
10. Portable.
11. Comfortable.
12. Easy to use.
13. Durable.
14. Economical.
15. Attractive.
16. Efficient.
17. Effective.

Although embodiments of the invention have been shown and described, it is to be understood that various modifications, substitutions, and rearrangements of equipment, instruments, devices, parts, components, and/or process (method) steps, can be made by those skilled in the art without departing from the novel spirit and scope of this invention.

What is claimed is:

1. A photoacoustic spectroscopy (PAS) system for remote sensing of a remote target comprising chemicals providing explosives, comprising:
   a tunable laser for transmitting optical energy comprising laser pulses at a selected frequency to the remote target and causing acoustic signals to be emitted from the target;
   a pulse generator comprising a chopper operating at a frequency selected on the basis of background noise for generating pulses to said tunable laser;
   a sensor for detecting acoustical signals from the target;
   a parabolic reflector for receiving acoustic signals from the target and focusing the acoustic signals to a focal area comprising said sensor;
   a cylindrical resonator for reducing acoustic interference and amplifying the acoustic signals, said cylindrical resonator providing an acoustic reverberant resonator comprising a cylindrical tube having an open end and a partially blocked end, the open end of the cylindrical tube being positioned at the local length of the parabolic reflector, the cylindrical tube being elongated and extending a length, the length of the cylindrical tube being adjustable to match a resonance condition in which the length of the cylindrical tube is equal to a multiple number of half acoustic wavelength according to the formula $l=n\lambda/2$ wherein
   l=length of the cylindrical tube
   n=integer
   $\lambda$=wavelength
   and the wavelength is equal to the sound velocity divided by a laser chopper frequency; and
   data acquisition and analysis equipment operatively connected and cooperating with said sensor, reflector, resonator, tunable laser, and pulse generator, for determining information about the target.

2. A photoacoustic spectroscopy (PAS) system for remote sensing of a remote target comprising chemicals providing explosives, comprising:
   a tunable laser for transmitting optical energy comprising laser pulses at a selected frequency to the remote target and causing acoustic signals to be emitted from the target;
   a pulse generator comprising a chopper operating at a frequency selected on the basis of background noise for generating pulses to said tunable laser;
   a sensor for detecting acoustical signals from the target;
   a reflector for receiving acoustic signals from the target and focusing the acoustic signals to a focal area comprising said sensor;
   a resonator for reducing acoustic interference and amplifying the acoustic signals;
   data acquisition and analysis equipment operatively connected and cooperating with said sensor, reflector, resonator, tunable laser, and pulse generator, for determining information about the target; and
   wherein said resonator comprises an acoustic reverberant resonator comprising a cylindrical tube having an open end and a partially blocked end, said reflector comprising a parabolic reflector having a focal length, the open end of the cylindrical tube being positioned at the focal length of the parabolic reflector, an acoustic transducer providing a microphone positioned in the cylindrical tube, and the cylindrical tube being elongated and extending a length, the length of the cylindrical tube being adjustable to match a resonance condition in which the length of the cylindrical tube is equal to a multiple number of half acoustic wavelength according to the formula $l=n\lambda/2$ wherein
   l=length of the cylindrical tube
   n=integer
   $\lambda$=wavelength
   and the wavelength is equal to the sound velocity divided by a laser chopper frequency.

3. A PAS system in accordance with claim 2 wherein:
   said tunable laser is a carbon dioxide ($CO_2$) infrared (IR) laser; and
   said chemicals providing explosives are selected from the group consisting of nitroglycerine (NG), ethylene glycol dinitrate (EGNG), dinitroltoluene (DNT), trinitrotoluene (TNT), and ammonium nitrate ($NH_4NO_3$).

4. A PAS system in accordance with claim 2 wherein said parabolic reflector has a diameter proportional to a distance to the target.

5. A PAS system in accordance with claim 2 wherein said resonator comprises a cylindrical tube resonator having a resonant frequency equaling the laser chopper frequency.

6. A photoacoustic spectroscopy (PAS) process for remote sensing of a remote target comprising chemicals providing explosives, comprising:
   providing an open-field acoustic resonator comprising an acoustic reverberant resonator with a cylindrical tube having an open end and a partially blocked end, and a parabolic reflector having a focal length, positioning the open end of the cylindrical tube at the focal length of the parabolic reflector, positioning an acoustic transducer in the cylindrical tube, adjusting the length of the cylindrical tube to correspond to a resonance condition in which the length of the cylindrical tube is equal to a multiple number of half acoustic wavelength according to the formula $l=n\lambda/2$ wherein
   l=length of the cylindrical tube
   n=integer
   $\lambda$=wavelength
   and the wavelength is equal to the sound velocity divided by a laser chopper frequency;
   transmitting optical energy comprising laser pulses at a selected frequency from a tunable laser in cooperation with a pulse generator comprising a chopper to the remote target comprising the chemicals providing the explosives, said chemicals being in a state selected from the group consisting of gases, liquids, solids, and combinations thereof;
   emitting acoustic signals from the target;
   the acoustic signals resonating at the laser chopper frequency or the harmonics of the laser;
   receiving acoustic signals from the target on the parabolic reflector;
   focusing the acoustic signals to the focal area at the open-field acoustic resonator;
   detecting the acoustic signals with the open-field acoustic resonator that is resonating at the laser chopper frequency or the harmonics of the laser;
   adjusting the resonator to optimize intensity of the acoustic signal; and determining information about the target with data acquisition and analysis equipment.

7. A PAS process in accordance with claim 6 wherein:
said chemicals providing the explosives are selected from the group consisting of nitroglycerine (NG), ethylene glycol dinitrate (EGNG), dinitroltoluene (DNT), trinitrotoluene (TNT), and ammonium nitrate ($NH_4NO_3$).

* * * * *